United States Patent
Gogolin

(10) Patent No.: US 8,114,181 B2
(45) Date of Patent: Feb. 14, 2012

(54) REFLUX TRAP DEVICE

(75) Inventor: Gary Gerard Gogolin, St. Petersburg, FL (US)

(73) Assignee: Bovie Medical Corporation, St. Petersburg, FL (US)

( * ) Notice: Subject to any disclaimer, the term of this patent is extended or adjusted under 35 U.S.C. 154(b) by 483 days.

(21) Appl. No.: 12/319,031

(22) Filed: Dec. 31, 2008

(65) Prior Publication Data

US 2010/0162893 A1  Jul. 1, 2010

(51) Int. Cl.
*A61M 25/00* (2006.01)
*A61F 5/44* (2006.01)

(52) U.S. Cl. ............. 55/385.1; 55/462; 604/45; 606/40

(58) Field of Classification Search .......... 55/337, 55/413, 418, 458, 459.1, 462, 463, 331, 336, 55/414, 416, 385.1, 503, 505; 606/40; 604/33, 604/45, 264; 95/273, 286
See application file for complete search history.

(56) References Cited

U.S. PATENT DOCUMENTS

| 540,539 | A | * | 6/1895 | Conness | 55/336 |
|---|---|---|---|---|---|
| 1,171,530 | A | * | 2/1916 | Michaels | 55/436 |
| 3,403,497 | A | * | 10/1968 | Vander Mey | 95/210 |
| 6,080,228 | A | * | 6/2000 | Okada et al. | 96/189 |
| 6,090,175 | A | * | 7/2000 | Richard | 55/337 |
| 6,099,523 | A | * | 8/2000 | Kim et al. | 606/40 |
| 7,258,712 | B2 | * | 8/2007 | Schultz et al. | 55/385.1 |
| 7,311,707 | B2 | * | 12/2007 | Hagg et al. | 606/49 |
| 7,335,199 | B2 | * | 2/2008 | Goble et al. | 606/49 |
| 7,431,748 | B2 | * | 10/2008 | Vandrak et al. | 55/463 |
| 7,799,104 | B2 | * | 9/2010 | Valentini | 55/337 |
| 7,959,698 | B2 | * | 6/2011 | Schultz et al. | 55/385.1 |
| 7,979,957 | B2 | * | 7/2011 | Meyer | 15/347 |
| 2003/0150195 | A1 | * | 8/2003 | Chang et al. | 55/385.1 |
| 2004/0128962 | A1 | * | 7/2004 | Jeanfreau | 55/385.1 |
| 2007/0137484 | A1 | * | 6/2007 | Roberts | 95/273 |
| 2007/0225700 | A1 | * | 9/2007 | Kuhner | 606/40 |
| 2007/0245699 | A1 | * | 10/2007 | Landman et al. | 55/385.1 |
| 2009/0000484 | A1 | * | 1/2009 | Schaedlich et al. | 96/256 |
| 2011/0041468 | A1 | * | 2/2011 | Schultz et al. | 55/385.1 |

\* cited by examiner

*Primary Examiner* — Duane Smith
*Assistant Examiner* — Minh-Chau Pham
(74) *Attorney, Agent, or Firm* — Arthur W. Fisher, III

(57) ABSTRACT

A reflux trap for use in a plasma generator and delivery system to prevent back flow of fluid and debris from a patient during a surgical procedure including a trap housing having a proximal diffuser chamber and a distal deflection chamber with a collection area separated by a baffle disposed within the trap housing including a diffuser member disposed in the proximal diffuser chamber to diffuse gas through a gas flow aperture to the surgical site on the patient and a deflection member disposed in the distal deflection chamber to deflect fluid and debris away from the gas flow aperture to the collection area to prevent fluid and debris from migrating into the proximal diffuser chamber to isolate the plasma generator against back flow of fluid and debris from the patient.

20 Claims, 4 Drawing Sheets

REFLUX TRAP DEVICE

CROSS-REFERENCE

This application claims priority based upon provisional application filed Dec. 5, 2008 for Inventor Gary Gerard Gogolin, entitled Reflux Trap Device.

BACKGROUND OF THE INVENTION

1. Field of the Invention

A reflux trap for use in a plasma generator and delivery system to prevent back flow of fluids and debris from a patient to the plasma generator during a surgical procedure.

2. Description of the Prior Art

High frequency electrical energy has been widely used in surgery. Tissue is cut and bodily fluids are coagulated using electrosurgical energy.

Electrosurgical instruments generally comprise "monopolar" devices or "bipolar" devices. Monopolar devices comprise an active electrode on the electrosurgical instrument with a return electrode attached to the patient. In monopolar electrosurgery, the electrosurgical energy flows through the active electrode on the instrument through the patient's body to the return electrode. Such monopolar devices are effective in surgical procedures where cutting and coagulation of tissue are required and where stray electrical currents do not pose a substantial risk to the patient.

Bipolar devices comprise an active electrode and a return electrode on the surgical instrument. In a bipolar electrosurgical device, electrosurgical energy flows through the active electrode to the tissue of a patient through a short distance through the tissue to the return electrode. The electrosurgical effects are substantially localized to a small area of tissue that is disposed between the two electrodes on the surgical instrument. Bipolar electrosurgical devices have been found to be useful with surgical procedures where stray electrical currents may pose a hazard to the patient or where other procedural concerns require close proximity of the active and return electrodes. Surgical operations involving bipolar electrosurgery often require methods and procedures that differ substantially from the methods and procedures involving monopolar electrosurgery.

Gas plasma is an ionized gas capable of conducting electrical energy. Plasmas are used in surgical devices to conduct electrosurgical energy to a patient. The plasma conducts the energy by providing a pathway of relatively low electrical resistance. The electrosurgical energy will follow through the plasma to cut, coagulate, desiccate, or fulgurate blood or tissue of the patient. There is no physical contact required between an electrode and the tissue treate.

A disadvantage of common to plasma generators resides in the fact that during insertion of the probe into the body cavity or after a probe has already been inserted the inert gas, as well as fluids and/or debris from the patient may flow back into the plasma generator system. As a result, various components may become contaminated.

U.S. Patent application publication No. U.S. 2007/0225700 A1 relates to an apparatus for argon-plasma coagulation in which working gas is supplied to a tissue to be treated by feeding the working gas flows out the distal end of the gas-supply devices. This apparatus for argon-plasma coagulation further comprises structure to prevent contamination of the gas-supply devices by working gas, bodily gases and/or bodily liquids including at least one obstructor to obstruct a flow of gas and/or liquid into the gas-supply devices against the supply-flow direction.

U.S. Pat. No. 7,311,707 discloses a connecting device for an electrosurgical instrument comprising at least one gas supply line and one power supply line. The connecting device comprises a housing into which passes the gas supply line including the power supply line disposed therein. The connecting device include a branching device located in the housing, and by way of which the power supply line is diverted out of the gas supply line in order to form a gas-connection end piece and a power-connection end piece. A plug is fixed to the housing to form a socket in an appliance or to connecting leads running to the appliance. The gas-connection end piece and the power-connection end piece are coupled to the plug and a filter disposed within the housing in the gas-connection end piece.

U.S. Pat. No. 7,431,748 shows a separation device for the removal of impurities extracted from a flexible conduit from a fuel such as liquefied petroleum gas having a housing with an inlet and an outlet and a means for channeling the fuel from the inlet onto an impingement surface in fluid communication with the fuel stream to condense the impurities. A gravity separation means collects the impurities removed from the fuel channeled into an outlet.

Additional examples of the prior art are found in; U.S. Pat. No. 191,100: U.S. Pat. No. 540,539; U.S. Pat. No. 1,171,530; U.S. Pat. No. 3,403,497 and DE 0,056,496.

SUMMARY OF THE INVENTION

The present invention relates to a reflux trap for use in a plasma generator and delivery system to prevent back flow of fluids and debris from a patient to the plasma generator.

The plasma generator and delivery system comprises an electrosurgical generator coupled to an inert gas source and a surgical probe coupled to the output of the electrosurgical generator, an electrode disposed within a gas feed conduit terminating in an ingiter tip to receive radio frequency power from the electrosurgical generator.

The reflux trap is disposed in fluid transfer communication the with gas feed conduit to prevent the inert gas, bodily fluids such as blood or body gases originating in the tissue and debris from flowing back into the electrosurgical generator.

More specifically, the reflux trap comprises a trap housing including a proximal diffuser chamber and a distal deflector chamber separated by a baffle disposed within the trap housing.

The baffle comprises a centrally disposed inner baffle member including a baffle element or base and at least one gas flow aperture. The baffle further includes a diffuser member including an inclined surface extending from the baffle element or base into the proximal diffuser chamber such that the inert gas fed into the diffuser chamber from the inert gas source impigns on the inclined surface and is directed or diffused through the gas flow aperture into and through the distal deflection chamber to the surgical site on the patient and a deflection member including an inclined surface extending from the baffle element or base into the distal deflection chamber such that fluids and debris flowing back into the distal deflection chamber from the patient impign on the inclined surface and are deflected to a collection area formed between the baffle and the deflection chamber where the fluids and debris are collected.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which.

Similar reference characters refer to similar parts throughout the several views of the drawings.

DETAILED DESCRIPTION OF THE INVENTION

Figure 1:
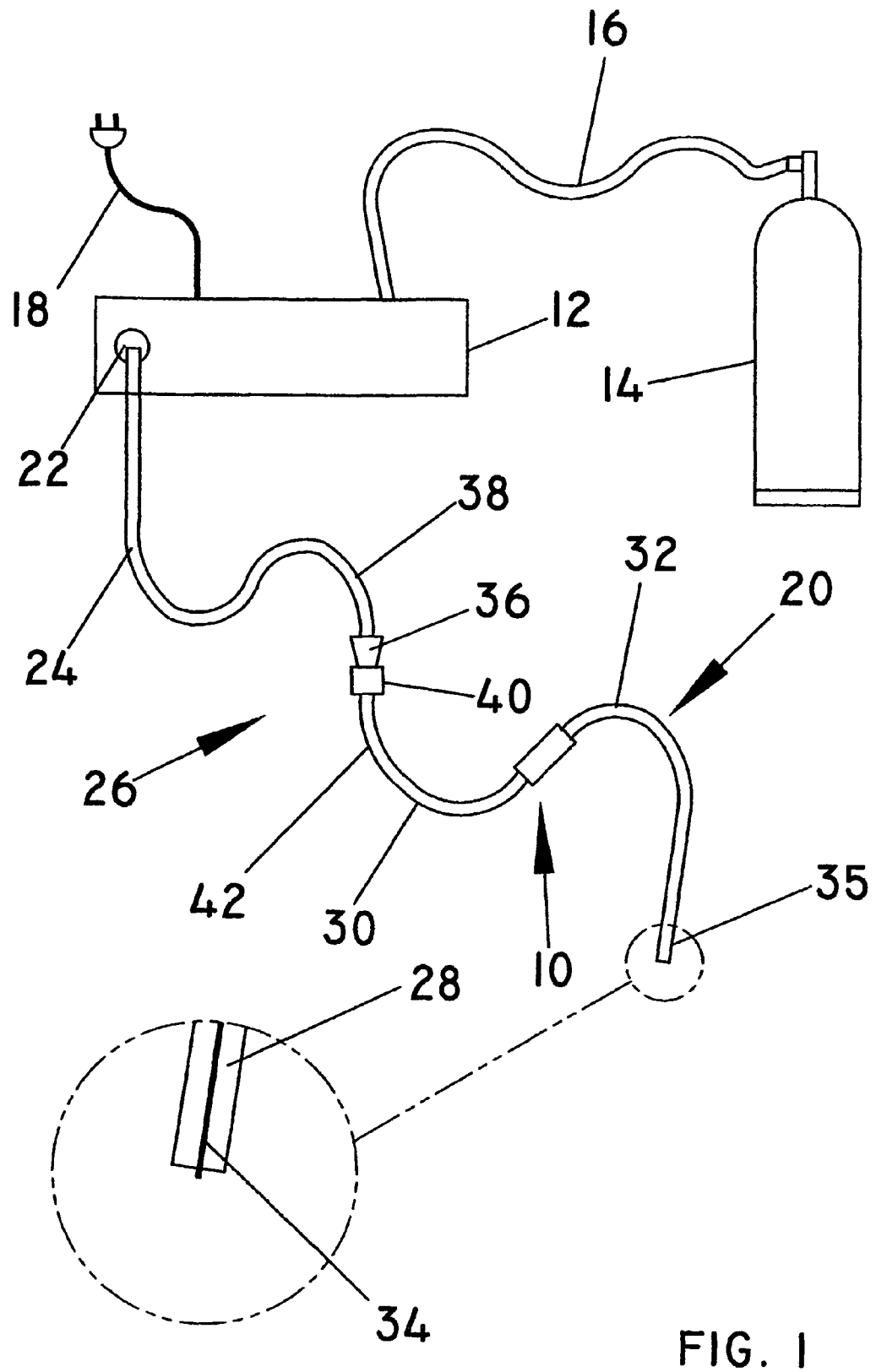
FIG. 1 is a schematic of the reflux trap of the present invention in combination with a plasma generator and delivery system.

As shown in FIG. 1, the present invention relates to a reflux trap generally indicated as 10 for use in a plasma generator and delivery system to prevent back flow of fluids and debris from a patient to the plasma generator.

The plasma generator and delivery system comprise an electrosurgical generator 12 coupled to an inert gas source such as argon 14 by a gas supply conduit 16 and to an external power source (not shown) by a conductor 18 and a surgical probe generally indicated as 20 coupled to the output 22 of the electrosurgical generator 12 by a proximal gas feed conduit 24 and a connector generally indicated as 26.

The surgical probe 20 comprises an electrode 28 disposed within a distal gas feed conduit including a first distal gas feed conduit section 30 and a second distal gas feed conduit section 32 terminating in an igniter tip 34 disposed at the distal portion 35 of the surgical probe 20 to receive radio frequency power from the electrosurgical generator 12 to generate plasma when the igniter tip 34 is in close proximity to grounded tissue of a patient. The connector 26 comprises a first connector member 36 affixed to the distal portion 38 of the proximal gas feed conduit 24 and a second connector member 40 affixed to the proximal portion 42 of the first distal gas feed conduit section 30.

The reflux trap 10 is disposed in fluid transfer communication with the distal gas feed conduit between the first distal gas feed conduit section 30 and the second distal gas feed conduit section 32 to prevent the inert gas, bodily fluids such as blood or body gases originating in the tissue and debris from flowing back into the electrosurgical generator 12.

As shown in FIGS. 2 through 5, the reflux trap 10 comprises a trap housing cooperatively formed by a first shell member 50 and a second shell member 52 mated or coupled together by a reduced diameter extension or longitudinally disposed projection 54 formed on the proximal end portion 56 of the second shell member 52 to press fit into the distal end portion 58 of the first shall member 50. A proximal diffuser chamber 60 and a distal deflection chamber 62 are separated by a baffle generally indicated as 64 disposed within the trap housing.

Figure 3:
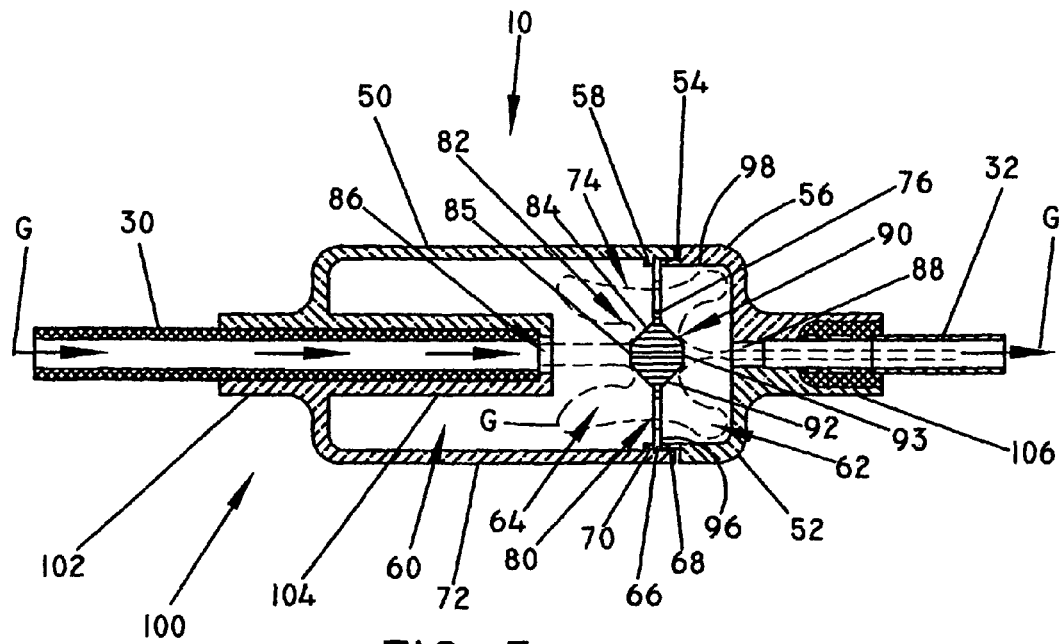
FIG. 3 is a cross-sectional side view of the reflux trap of the present invention showing gas flow to the patient.
Figure 4:
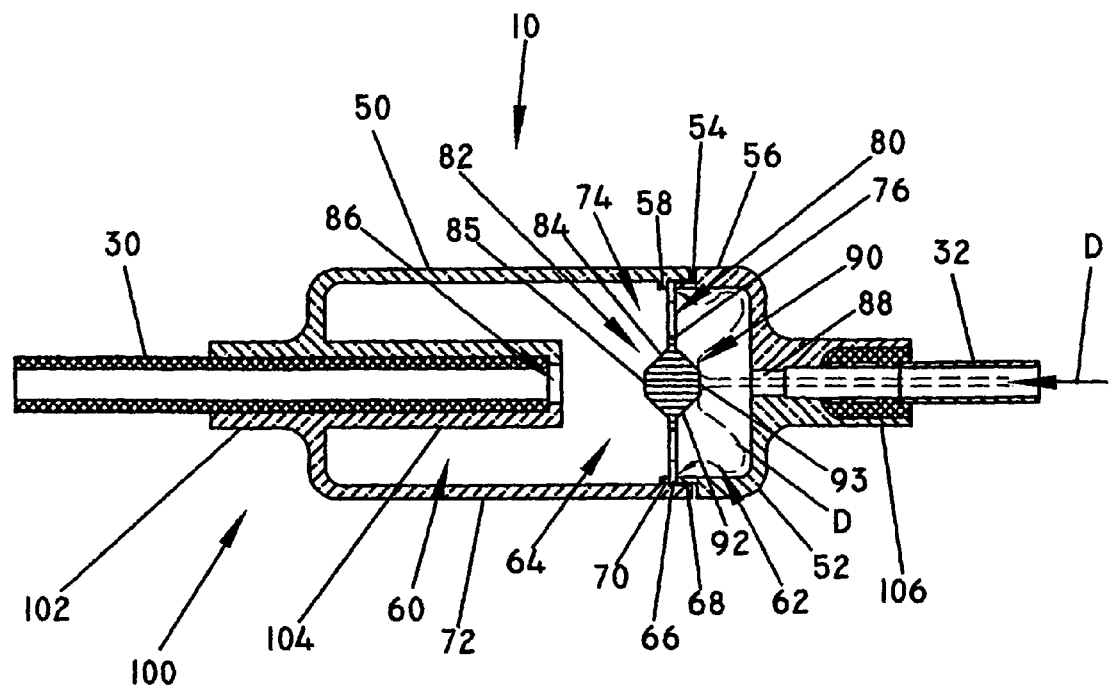
FIG. 4 is a cross-sectional side view of the reflux trap of the present invention showing back flow of fluids and/or debris from the patient.
Figure 5:
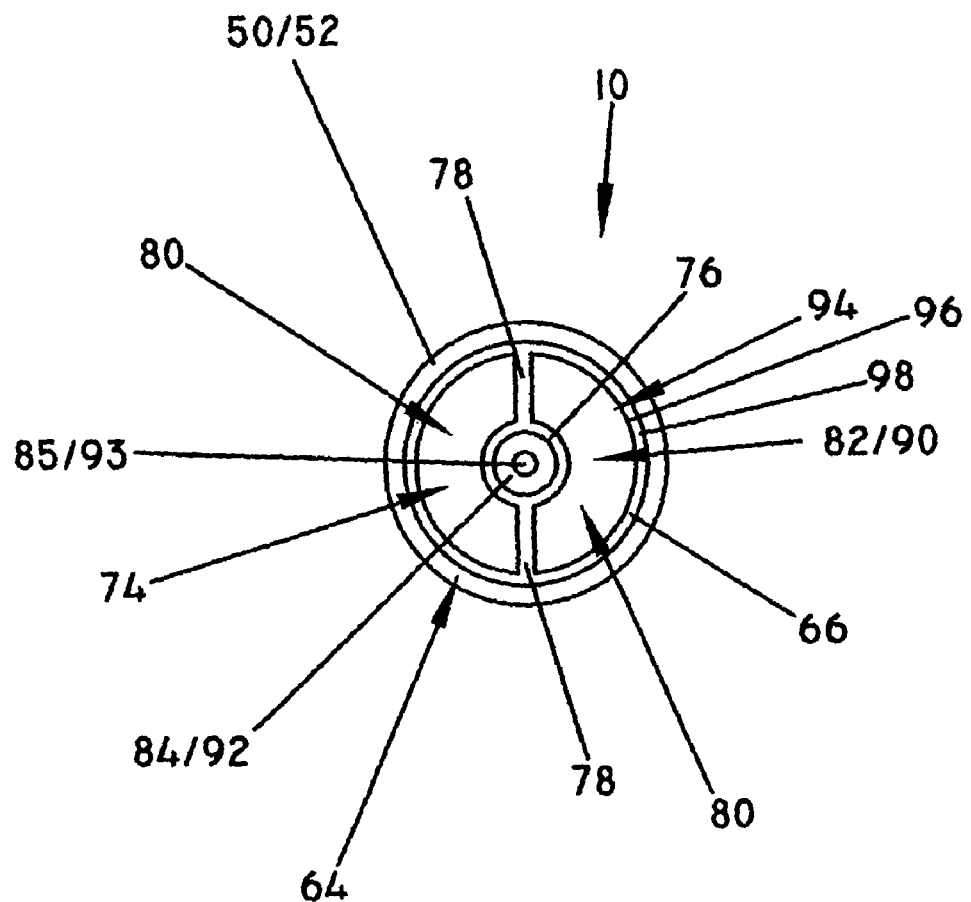
FIG. 5 is an end view of the reflux trap of the present invention.

As shown in FIGS. 3 through 5, the baffle 64 comprises an outer ring 66 sandwiched or mounted within the trap housing between the inner end 68 of the reduced diameter extension or longitudinally disposed projection 54 and a laterally disposed ledge 70 extending inwardly from the side wall 72 of the first shell member 50 and a centrally disposed inner baffle member generally indicated as 74 including a baffle element or base 76 interconnected to the outer ring 66 by a pair of interconnecting elements each indicated as 78 cooperatively forming a pair of gas flow apertures each indicated as 80. The baffle 64 further includes a substantially frustum conical diffuser member generally indicated as 82 including an inclined surface 84 terminating in a substantially flat or convex surface or trap 85 extending from the baffle element or base 76 into the proximal diffuser chamber 60 such that the inert gas G fed into the diffuser chamber 60 from the inert gas source 14 through a proximal gas inlet port 86 formed in the first shell member 50 of the trap housing impigns on the inclined surface 84 and the substantially flat or convex surface or tip 85 of the substantially frustum conical diffuser member 82 and directed or diffused through the gas flow apertures 80 into the distal deflection chamber 62 and through a distal gas outlet port 88 formed in the second shell member 52 of the trap housing to the surgical site on the patient (not shown) as shown in FIG. 3 and a substantially frustum conical deflection member generally indicated as 90 including an inclined surface 92 terminating in a substantially flat 93 or convex surface or tip extending from the baffle element or base 76 into the distal deflection chamber 62 such that fluids and debris D flowing back into the distal deflection chamber 62 from the patient (not shown) through the distal gas outlet port 88 impign on the inclined surface 92 and the substantially flat or convex surface or tip 93 and deflected to a collection area 94 formed at the intersection formed by the outer ring surface 96 and the inner wall 98 of the second shell member 52 where the fluids and debris D are collected.

Figure 2:
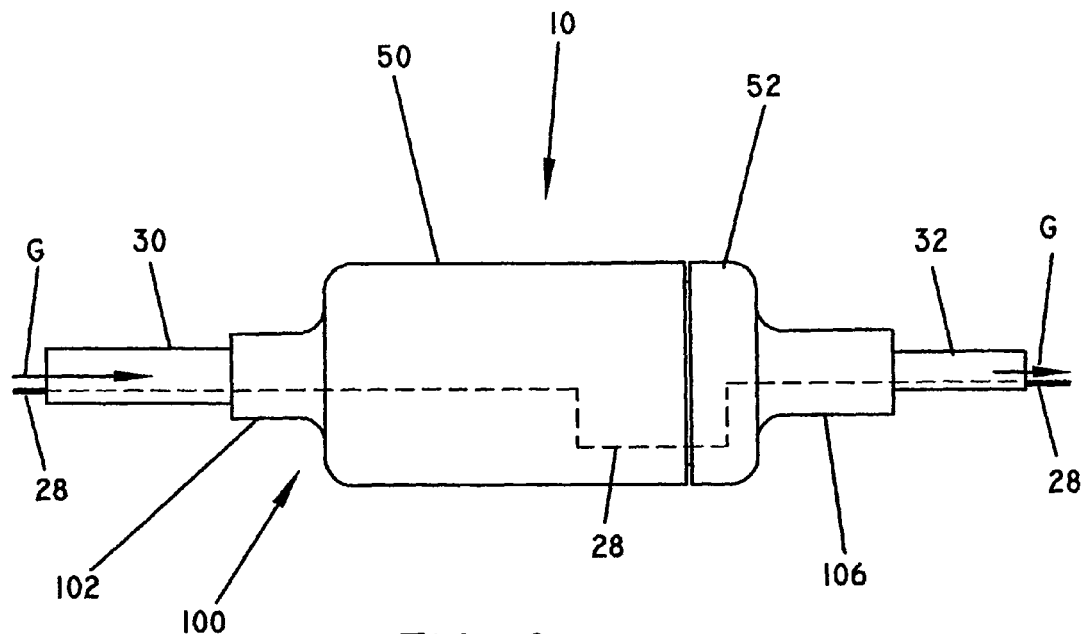
FIG. 2 is a side view of the reflux trap of the present invention.

As shown in FIGS. 2 through 4, the first distal gas feed section 30 is coupled to the first shell member 50 of the reflux trap 10 by a proximal coupler sleeve generally indicated as 100 including an outer coupler section 102 and an inner coupler section 104; while, the second distal gas feed section 32 is coupled to the second shell member 52 of the reflux trap 10 by a distal coupler sleeve 106.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

What is claimed is:

1. A reflux trap for use in a plasma generator and delivery system to prevent back flow of fluids and debris from a patient to the plasma generator during a surgical procedure comprising a trap housing including a proximal diffuser chamber and a distal deflection chamber having a collection area separated by a baffle disposed within said trap housing and having at least one gas flow aperture formed therethrough, a proximal inlet port and a distal outlet port formed on opposite end portions of said trap housing to feed gas to and from said trap housing through said proximal diffuser chamber, said gas flow aperture and said distal deflection chamber, said baffle further including a diffuser member disposed in said proximal diffuser chamber such that gas fed into said proximal diffuser chamber through said proximal inlet port impigns thereon and diffused through said gas flow aperture into said distal deflection chamber and through said distal outlet port to the surgical site on the patient and a deflection member disposed in said distal deflection chamber such that fluids and debris flowing back from the patient through said outlet port into said distal deflection chamber impign thereon and are deflected away from said gas flow aperture to said collection area preventing fluids and debris from migrating through said gas flow aperture into said proximal diffuser chamber isolating the plasma generator against back flow of fluid and debris from the patient.

2. A reflux trap and plasma generator and delivery system to prevent back flow of fluids and debris from a patient to the plasma generator during a surgical procedure comprising a trap housing including a proximal diffuser chamber and a distal deflection chamber having a collection area separated by a baffle disposed within said trap housing and having at least one gas flow aperture formed therethrough, a proximal inlet port and a distal outlet port formed on opposite end portions of said trap housing to feed gas to and from said trap housing through said proximal diffuser chamber, said gas flow aperture and said distal deflection chamber, said baffle further including a diffuser member disposed in said proximal diffuser chamber such that gas fed into said proximal diffuser chamber through said proximal inlet port impigns thereon and diffused through said gas flow aperture into said distal deflection chamber and through said distal outlet port to the surgical site on the patient and a deflection member disposed in said distal deflection chamber such that fluids and debris flowing back from the patient through said outlet port into said distal deflection chamber impign thereon and are deflected away from said gas flow aperture to said collection area preventing fluids and debris from migrating through said gas flow aperture into said proximal diffuser chamber isolating the plasma generator against back flow of fluid and debris from the patient, said plasma generator and delivery system comprising an electrosurgical generator including an output coupled to an inert gas source by a gas supply conduit and to an external power source by a conductor and a surgical probe coupled to the output of said electrosurgical generator by a proximal gas feed conduit, said surgical probe comprising an electrode disposed within a distal gas feed conduit including a first distal gas feed conduit section and a second distal gas feed conduit section terminating in an igniter tip disposed at the distal portion of said surgical probe to receive radio frequency power from said electrosurgical generator to generate plasma when said igniter tip is in close proximity to grounded tissue of a patient, said connector comprises a first connector member affixed to a distal portion of said proximal gas feed conduit and a second connector member affixed to a proximal portion of said first distal gas feed conduit section.

3. A reflux trap for use in a plasma generator and delivery system to prevent back flow of fluids and debris from a patient to the plasma generator during a surgical procedure comprising a trap housing including a diffuser chamber and a deflection chamber having a collection area separated by a baffle disposed within said trap housing and having at least one gas flow aperture formed therethrough, an inlet port and a outlet port formed on opposite end portions of said trap housing to feed gas to and from said trap housing through said diffuser chamber, said gas flow aperture and said deflection chamber, said baffle further including a diffuser member disposed in said diffuser chamber such that gas fed into said diffuser chamber through said inlet port impigns thereon and diffused through said gas flow aperture into said distal deflection chamber and through said outlet port to the surgical site on the patient and a deflection member disposed in said deflection chamber such that fluids and debris flowing back from the patient through said outlet port into said deflection chamber impign thereon and are deflected away from said gas flow aperture to said collection area preventing fluids and debris from migrating through said gas flow aperture into said diffuser chamber isolating the plasma generator against back flow of fluid and debris from the patient.

4. The reflux trap of claim 3 wherein said trap housing comprises a first shell member and a second shell member.

5. The reflux trap of claim 4 wherein said baffle comprises an outer ring mounted within said trap housing between said first shell member and said second shell member.

6. The reflux trap of claim 5 wherein said baffle comprises an outer ring mounted within said trap housing between said inner end of said reduced diameter longitudinally disposed projection and a laterally disposed ledger extending inwardly from a side wall of said first shell member and a centrally disposed Inner baffle member including a baffle element interconnected to said outer ring at least one interconnecting element to cooperatively form a gas flow aperture.

7. The reflux trap of claim 3 wherein said trap housing comprises a first shell member and a second shell member coupled together by a reduced diameter longitudinally disposed projection formed on a proximal end portion of said second shell member to press fit into a distal end portion of said first shell member.

8. The reflux trap of claim 7 wherein said baffle comprises an outer ring mounted within said trap housing between said inner end of said reduced diameter longitudinally disposed projection and a laterally disposed ledger extending inwardly from a side wall of said first shell member and a centrally disposed inner baffle member including a baffle element interconnected to said outer ring at least one interconnecting element to cooperatively form a gas flow aperture.

9. The reflux trap of claim 8 wherein said diffuser member includes an inclined surface extending from said baffle element into said diffuser chamber such that the inert gas fed into said diffuser chamber from the inert gas source through a proximal gas inlet port formed in said first shell member of said trap housing impigns on said inclined surface of said diffuser member and diffused through said gas flow aperture into said distal deflection chamber and through a distal gas outlet port formed in said second shell member of said trap housing to the surgical site on the patient.

10. The reflux trap of claim 9 wherein said diffuser member further includes a substantially convex surface at the tip of said diffuser member.

11. The reflux trap of claim 8 wherein said diffuser member comprises a substantially frustum conical diffuser member.

12. The reflux trap of claim 9 wherein said deflection member includes an inclined surface extending from said baffle element into said distal deflection chamber such that fluids and debris flowing back into said deflection chamber from the patient through said distal gas outlet port impign on said inclined surface and deflected to said collection area formed by said outer ring surface and the inner wall of said second shell member.

13. The reflux trap of claim 12 wherein said deflection member comprises a substantially frustum conical deflection member.

14. The reflux trap of claim 12 wherein said deflection member further includes a substantially convex surface at the tip of said deflection member.

15. The reflux trap of claim 3 wherein said diffuser member includes an inclined surface extending from said baffle element into said diffuser chamber such that the inert gas fed into said diffuser chamber from the inert gas source through a proximal gas inlet port formed in said first shell member of said trap housing impigns on said inclined surface said diffuser member and diffused through said gas flow aperture into said distal deflection chamber and through a distal gas outlet port formed in said second shell member of said trap housing to the surgical site on the patient and said deflection member includes an inclined surface extending from said baffle element into said deflection chamber such that fluids and debris flowing back into said distal deflection chamber from the patient through said distal gas outlet port impign on said inclined surface and deflected to a collection area formed by said outer ring surface and said second shell member where the fluids and debris are collected.

16. The reflux trap of claim 15 wherein said diffuser member further includes a substantially convex surface at the tip of said diffuser member.

17. The reflux trap of claim 15 wherein said said diffuser member comprises a substantially frustum conical diffuser member.

18. The reflux trap of claim 15 wherein said deflection member comprises a substantially frustum conical deflection member.

19. The reflux trap of claim 15 wherein said deflection member further includes a substantially convex surface at the tip of said deflection member.

20. The reflux trap of claim 3 wherein' said first distal gas feed section is coupled to said first shell member of said reflux trap by a proximal coupler sleeve including an outer coupler section and an inner coupler section, and said second distal gas feed section is coupled to said second shell member of said reflux trap by a distal coupler sleeve.

* * * * *